(12) United States Patent
Lintner (10) Patent No.: US 7,354,926 B2
(45) Date of Patent: Apr. 8, 2008

(54) MOLECULES DERIVED FROM NORAPORPHINE

(75) Inventor: Karl Lintner, Rambouillet (FR)

(73) Assignee: Sederma SAS (FR)

( * ) Notice: Subject to any disclaimer, the term of this patent is extended or adjusted under 35 U.S.C. 154(b) by 0 days.

(21) Appl. No.: 10/525,985

(22) PCT Filed: Jul. 29, 2003

(86) PCT No.: PCT/FR03/02400

§ 371 (c)(1),
(2), (4) Date: Sep. 15, 2005

(87) PCT Pub. No.: WO2004/024695

PCT Pub. Date: Mar. 25, 2004

(65) Prior Publication Data

US 2006/0110413 A1    May 25, 2006

(30) Foreign Application Priority Data

Aug. 30, 2002  (FR) .................................. 02 10810

(51) Int. Cl.
*A61K 31/473* (2006.01)
*C07D 221/18* (2006.01)
(52) U.S. Cl. ........................................ 514/284; 546/75
(58) Field of Classification Search ................ 514/284; 546/75
See application file for complete search history.

(56) References Cited

U.S. PATENT DOCUMENTS

| | | |
|---|---|---|
| 3,131,191 A | 4/1964 | Douglas et al. |
| 4,279,914 A * | 7/1981 | Maasbol et al. ............ 514/284 |
| 5,607,980 A | 3/1997 | McAtee et al. |
| 6,313,134 B1 * | 11/2001 | Su et al. ..................... 514/284 |

FOREIGN PATENT DOCUMENTS

| | | | |
|---|---|---|---|
| DE | 1145709 A1 | * | 10/2001 |
| EP | 0 040 074 A1 | | 11/1991 |
| EP | 0 848 041 A1 | | 6/1998 |
| FR | 1477048 A | | 4/1967 |
| FR | 2.091.516 A | | 1/1972 |
| FR | 2 315 991 A | | 1/1977 |
| FR | 2 465 780 A | | 3/1981 |
| FR | 2 482 128 A | | 11/1981 |
| WO | WO-83/01571 A1 | | 5/1983 |
| WO | WO-92/08685 A1 | | 5/1992 |
| WO | WO 99/16441 | * | 8/1999 |
| WO | WO 00/59466 | * | 10/2000 |
| WO | WO-00/62743 A2 | | 10/2000 |
| WO | WO 02/066000 | * | 8/2002 |

OTHER PUBLICATIONS

Cortes, D. et al.: Trivalvone, a new bisaporphine from bark of Trivalvone macrophylla. J. of Natural products, vol. 53, pp. 862-866, 1990.*
Hoshino, O. et al.: Studies on tetrahydroisoquinolines. Chem Pharm. Bull. vol. 27, pp. 3101-3105.*
Chen, K-S. et al.: Antiplatelet and vasorelaxing actions of some aporphinoids. Planta medica, vol. 62, pp. 133-136, 1996.*
Yu, S.: Thaliporphine selectively inhibits expression of the inducible, but not the constitutive, nitric oxide synthase. Biochem. Journal, vol. 303, pp. 289-294, 1994.*

* cited by examiner

*Primary Examiner*—Charanjit S. Aulakh
(74) *Attorney, Agent, or Firm*—Lerner, David, Littenberg, Krumholz & Mentlik, LLP (57) ABSTRACT

The invention concerns novel molecules derived from noraporphine, as well as cosmetic and dermopharmaceutical compositions containing one or several of said derivatives, alone or combined with a plant extract, in particular *glaucium flavum*, and particularly preparations for reducing pigmentation, with anti-ageing effect or for slimming.

6 Claims, 1 Drawing Sheet

FIGURE 1

MOLECULES DERIVED FROM NORAPORPHINE

SUMMARY OF THE INVENTION

The invention concerns novel molecules derived from noraporphine, as well as cosmetic and dermopharmaceutical compositions containing one or several of said derivatives, alone or combined with a plant extract, in particular *glaucium flavum*, and particularly preparations for reducing pigmentation, with anti-ageing effect or for slimming.

BACKGROUND OF THE INVENTION

The natural pigmentation of the skin stems from a mechanism that has now been clearly described: the melanocytes present in the stratum basale epidermidis produce melanin pigments which are synthesized in the melanosomes. Melanin synthesis (melanogenesis) increases under the action of UV radiation. The physiological function of tanning which ensues thus aims to protect the skin against UV radiation.

Various dysfunctions in the melanin production mechanism (due to an excess of external aggressions, hormonal disturbances or aging) induce the emergence of brown spots, particularly in the form of ephelides (freckles), and solar or senile lentigines.

Modifying the natural pigmentation of the skin is a desire shared by European, Asian and American women, although the underlying rationales differ: a white complexion is considered beautiful by some, while others seek to attenuate senile lentigo, considered to reveal aging. In Asia, as is the case in Europe and America, controlling skin pigmentation is thus a sensitive subject and the object of considerable demand.

Three key enzymes are involved in melanogenesis: tyrosinase and tyrosine-related proteins (TRP-1 and TRP-2). All three are glycoproteins located in the melanosome membrane. Out of the three, tyrosinase is the limiting enzyme in that it catalyzes the first two stages in pigment formation: ortho-hydroxylation of tyrosine to yield L-DOPA, then oxidation of the latter to yield dopaquinone. TRP-1 and TRP-2 are reported to intervene, in part, by stabilizing tyrosine hydroxylase.

In addition, it is known that stimulation of melanogenesis involves increasing intracellular cAMP levels. cAMP regulates the action of a protein kinase, PKC-b, whose ability to phosphorylate tyrosinase is determinant in melanin synthesis. In support of this mechanism, it has been observed that UV radiation very significantly increases PKC-b in cultured melanocytes.

Lastly, the role played by intracellular calcium in melanocyte metabolism is also undoubtedly to be taken into account.

To influence skin pigmentation, it is therefore possible to envisage degrading melanin, offering melanogenesis inhibitors which interact with the various targets described above, or even inhibiting the distribution of melanin in the epidermal cell layers.

However, the most frequently selected target is undoubtedly tyrosine hydroxylase, since it constitutes a limiting step in the process.

For a considerable time, depigmentation or lightening the skin was achieved using very potent products such as hydroquinone, sulfur- or non-sulfur-containing phenolic compounds and ascorbic acid. However, those products were not devoid of irreversible hypopigmentation effects and induced irritation. All those products are to be used in an efficacy/safety context that is not appropriate for cosmetics.

In the cosmetic field, the problem was tackled by using various retinoid derivatives, AHA, kojic acid and arbutin. The good results obtained in vitro on cellular cultures are seldom reproduced for use in vivo.

Hydroquinone, arbutin and kojic acid were developed for their competitive inhibition of tyrosinase or inhibition of the catalytic activity indispensable to tyrosinase function by chelation of copper ions. However, those products are difficult to use and may induce adverse effects.

There is thus a strong demand for innovative cosmetic products that are effective in vivo and non-toxic.

Increasing the intracellular rate of cAMP is also the objective of the slimming active ingredients. Indeed intracellular cAMP is essential to activate the glycerol release via adipocyte lipase (HSL): by this way, there is a depletion of cell lipid materials, and hence a decrease in cell volume.

Following the generation of slimming active substances based on direct activation of the lipolysis via phosphodiesterase inhibition (e.g., caffeine), more sophisticated products emerged. Those products address either to the stimulation of membrane receptors and their systems of intracellular transduction (protein G), or to their inhibition (receptors alpha and neuropeptide Y). All these approaches aim at increasing the rate of intracellular cAMP.

However, an original and alternative route may exist even opposite with the system supporting the increase of intracellular pool of cAMP with an aim of lipolysis stimulation.

The central role played by the intracellular calcium in the metabolism of the pre-adipocyte and the mature adipocyte is a well documented phenomenon and it is clear that the $Ca^{++}$ takes part in several different ways in the installation of the fatty mass. Whereas this one, by an entering flow, inhibits the initial differentiation of pre-adipocytes by decreasing the triglycerides storage, it plays an opposite role in the final phase of differentiation like in the mature adipocyte by supporting the lipogenesis. To understand this phenomenon it should be known that there is a structural and functional connection between the membrane sites of the calcium entry and the adenylate cyclase.

By blocking calcium entry, the initial phase of differentiation is supported because the calcium-dependent postmitosis inhibition is then raised, and the final phase of differentiation is disadvantaged by blocking the lipogenesis.

It is well-known in Pharmacology that an entering calcium flow supported by norepinephrine ($\alpha$-adrenergic agonist) can be blocked by $\alpha_1$ antagonists such as prazosine and to a lesser extent by $\beta_1$-adrenergic antagonists. In addition, it is known that within a adipocyte population more than 60% of the cells express the $\alpha_1$ et $\beta_1$-adrenergic receptors.

This brake by adrenergic antagonists is translated in pre-adipocyte and the adipocyte by a differentiation markers reduction which are glycerol-3-phosphate dehydrogenase (G-3-PDH) and "peroxisome proliferator-activated receptor gamma" (PPARγ), as well as by a triglycerides storage reduction.

To fight effectively against the pads and capitons, the consumers push cosmetic industry with the development of increasingly powerful active ingredients.

BRIEF SUMMARY OF THE INVENTION

We discovered, quite surprisingly, that molecules which contain a core 1,2,9,10-tetrahydroxy-noraporphine in their structure have at least one of, and often at the same time, a strong capacity of melanogenesis inhibition and an antioxidant effect, as well as a significant activity against lipogenesis.

The invention constituting the subject of the present application resides in the fact that we have discovered and demonstrated that the compounds derived from noraporphines of general formula I can do one or more of: reduce melanin production in an effective and non-toxic manner, block the lipogenesis, and present antioxidant activity. The new derivatives that constitute the subject of the present patent application are also of value in that they have good bioavailability, solubility, activity, stability or toxicological profile.

The present invention thus addresses the compounds with the following general formula I, derivatives from 1,2,9,10-tetrahydroxy-noraporphine:

I in which the groups $R^1$, $R^2$, $R^3$, $R^4$ and $R^5$, which may be the same or different, each one of them includes a hydrogen atom, an alkyl, aryl, aralkyl, acyl, sulfonyl or sugar group.

Compounds of general formula I according to the invention may exist in free form or in the form of a salt formed with an acid that is acceptable in cosmetic terms. The present invention includes both the free forms and the salts of those compounds.

One aspect of the present invention concerns neither 2,9-dihydroxy-1,10-dimethoxy-6-methyl-noraporphine (formula I, $R^1$=H, $R^2$=$R^3$=$CH_3$, $R^4$=H, $R^5$=$CH_3$), neither 1,2,10-trimethoxy-9-hydroxy-6-methyl-noraporphine (formula I, $R^1$=$R^2$=$R^3$=$CH_3$, $R^4$=H, $R^5$=$CH_3$), nor 1,2,9,10-tetramethoxy-6-methyl-noraporphine (formula I, $R^1$=$R^2$=$R^3$=$R^4$=$R^5$=$CH_3$), already described substances. This proviso is preferably limited to only the free base form of these compounds and does not exclude their salts or substantially pure optical isomers thereof.

Another aspect of the present invention is cosmetic or dermopharmaceutical compositions including a compound of formula I, including the three compounds described immediately above, and at least one of a carrier, a cosmetic ingredient commonly used in the cosmetic industry, active substances or a principal adjuvant. Methods of using these cosmetics and dermopharmaceuticals for amongst others, reducing skin pigmentation, reducing signs of aging, and slimming are also contemplated.

DETAILED DESCRIPTION OF PREFERRED EMBODIMENTS

In the context of the present invention, the term 'acid acceptable in cosmetic terms' is taken to mean any non-toxic acid, including organic and inorganic acids. Such acids include acetic, para-aminobenzoic, ascorbic, aspartic, benzenesulfonic, benzoic, bismethylene salicylic, hydrobromic, hydrochloric, cinnamic, citraconic, citric, ethanedisulfonic, fumaric, gluconic, glutamic, glyconic, itaconic, lactic, maleic, malic, mandelic, methanesulfonic, mucic, nitric, oxalic, palmitic, pamoic, pantothenic, phosphoric, propionic, salicylic, stearic, succinic, sulfamic, sulfuric, tartaric and para-toluenesulfonic acid. Hydrochloric acid and acetic acid are particularly preferred.

In the context of the present invention, the terms 'alkyl" and 'alkyl group' are taken to mean any alkyl group of 1 to 20 carbon atoms, linear or branched, substituted or not substituted (substituted, in particular, by an alcohol, carboxylic acid or amine) and saturated or unsaturated. In particular, an alkyl group may be the methyl group.

In the context of the present invention, the terms 'aryl' and 'aryl group' are taken to mean one or several aromatic rings, each consisting of 5 to 8 carbon atoms that may abut or be fused and may or may not be substituted. In particular, the aryl groups may be phenyl or naphthyl groups and the substituents, halogen atoms, alkoxy groups as defined above, alkyl groups as defined above or nitro groups.

In the context of the present invention, the terms 'aralkyl' and 'aralkyl group' are taken to mean any aryl group as defined above, bounded via an alkyl group as defined above. In particular, an aralkyl group is the benzyl group.

In the context of the present invention, the terms 'acyl' and 'acyl group' are taken to mean any group —C=$OR^6$ in which $R^6$ may be an alkyl, aryl, aralkyl or amine group as defined above. In particular, an acyl group may be the acetyl group ($R^6$=—$CH_3$).

In the context of the present invention, the terms 'amine' and 'amine group' is taken to mean any group —$NR^7R^8$, in which $R^7$ and $R^8$ may be the same or different and each consists in a hydrogen atom or an alkyl, aryl, aralkyl, acyl, sulfonyl or sugar group as defined above.

In the context of the present invention, the terms 'sulfonyl' and 'sulfonyl group' are taken to mean any group —$SO_2R^9$, in which $R^9$ may be an alkyl, aryl, aralkyl, alkoxy or amine group as defined above. In particular, sulfonyl groups may be mesyl ($R^9$=—$CH_3$), triflyl ($R^9$=—$CF_3$) or tosyl ($R^9$=-Ph-$CH_3$) groups In the context of the present invention, the terms 'alkoxy' and 'alkoxy group', are taken to mean any —$OR^{10}$ in which $R^{10}$ may be an alkyl, aryl, aralkyl, acyl, sulfonyl or sugar group as defined above.

In the context of the present invention, the terms 'sugar' and 'sugar group' are taken to mean any hexose, -ose or -oside group. In particular, the sugar groups may be glucose, arabinose, fructose, galactose, mannose, maltose, lactose, sucrose or cellobiose groups.

The compounds according to the present invention may contain a center of asymmetry and thus exist in the form of optical isomers. The present invention covers each of the optical isomers separately and any mixture of those isomers.

A particularly advantageous compound according to the invention is 2,9-diacetyloxy-1,10-dimethoxy-6-methyl-noraporphine (formula II=formula I in which $R^1$=$R^4$=—$COCH_3$, $R^2$=$R^3$=$CH_3$, $R^5$=$CH_3$).

II

To obtain one or more of the effects described herein, the compounds of general formula I useful in the cosmetic and dermopharmaceutical compositions, may be found by any source of supply, in particular by chemical synthesis, enzymatic synthesis, by one of many biotechnology processes, by plant extraction or any other suitable means that allow to obtain them at reasonable cost in the finished product and to use them industrially.

In the case of a vegetable origin, any plant species can be appropriate, provided that the extract obtained from any part of the plant, includes one or several compounds derivating from the general formula I as described herein. A plant which contains alkaloids of the family of general formula I, and in particular 1,2,9,10-tetramethoxy-6-methyl-noraporphine (formula I, $R^1=R^2=R^3=R^4=R^5=CH_3$), is *glaucium flavum*.

*Glaucium flavum*, of the papaveraceae family, is an European plant of average size (0.5 meters approximately), with the slow growth and yellow hermaphrodites flowers. It blooms from June to August, and its seeds mature from August till September.

Extraction solvents can be selected among water, propylene glycol, butylene glycol, glycerin, polyethylene glycol, methylic and/or ethylic diglycol ethers, cyclic polyols, ethoxylated or propoxylated diglycols, alcohols (methanol, ethanol, propanol, butanol), or any mixture of those solvents.

In addition, it is possible to carry out extracts of *glaucium flavum* by other processes as, for example, steeping, simple decoction, lixiviation, extraction under reflux, supercritical extraction, extraction with ultrasounds or micro-waves or finally with countercurrent technology, without this list being restrictive As for 2,9-dihydroxy-1,10-dimethoxy-6-methyl-noraporphine, 1,2,10-trimethoxy-9-hydroxy-6-methyl-noraporphine and 1,2,9,10-tetramethoxy-6-methyl-noraporphine, although known as natural substances, they were never described as active ingredients of any cosmetic or dermopharmaceutical composition.

Thus the present invention also relates to the cosmetic and dermopharmaceutical compositions containing one or more compounds above of general formula I, including 2,9-dihydroxy-1,10-dimethoxy-6-methyl-noraporphine (formula I, R1=H, R2=R3=CH3, R4=H, R5=CH3), and 1,2,10-trimethoxy-9-hydroxy-6-methyl-noraporphine (formula I, R1=R2=R3=CH3, R4=H, R5=CH3) and 1,2,9,10-tetramethoxy-6-methyl-noraporphine (formula I, R1=R2=R3=R4=R5=CH3), alone or in association, and a carrier, an active substance, and/or a principal adjuvant.

These three last molecules, namely 2,9-dihydroxy-1,10-dimethoxy-6-methyl-noraporphine, 1,2,10-trimethoxy-9-hydroxy-6-methyl-noraporphine and 1,2,9,10-tetramethoxy-6-methyl-noraporphine may be obtained by any of the methods previously described including synthesis, or by plant extraction The compounds of general formula I are used in cosmetic and dermopharmaceutical compositions as per the invention at concentrations which may range from 0.0001 (w/w) to 50% (w/w) but preferably between 0.001 (w/w) and 20% (w/w).

In the cosmetic and dermopharmaceutical compositions, it can be advantageous to associate compounds derived from the general formula I with an extract of plant, and in particular an *glaucium flavum* extract such as defined above.

The *glaucium flavum* extract can be used either in liquid form, or in dry form obtained by precipitation, atomization, evaporation or lyophilization. The quantity of plant extract, such as *glaucium flavum* extract, to be incorporated in the cosmetic or dermopharmaceutical preparations lies between 0.1 and 100% (w/w), preferentially between 0.1 and 10% in weight of the final total composition.

The incorporation of the plant extracts, such as *glaucium flavum* extracts, whatever its origin, in the cosmetic compositions is realized by any type of process classically used in cosmetology and dermopharmacy.

The compositions are for example lotions, milks or emollient creams; milks or creams for skin care or hair care; make-up-removing cleansing creams, lotions, or milks; foundation tint bases; sun-screen lotions, milks, or creams; artificial suntan lotions, milks, or creams; shaving creams and foams; aftershave lotions; shampoos, lipsticks, mascaras, or nail varnishes.

These compositions can also be presented in the form of lipsticks intended to apply colour or to protect the lips from cracking, or of make-up products for the eyes or tints and tint bases for the face.

When the compositions according to the invention are presented in the form of water-in-oil or oil-in-water emulsions, the fatty phase may include a mixture of fatty substances obtained by extraction or synthesis, with at least one oil and possibly another fatty substance. The fatty phase of the emulsions may constitute 5 to 60% of the total weight of the emulsion. Note that the fatty phase is made up of one or more principal adjuvant or carrier.

The aqueous phase of the said emulsions constitutes preferably 30 to 85% of the total weight of the emulsion. The proportion of the emulsifying agent may be between 1 and 20%, and preferably between 2 and 12% of the total emulsion weight. When the compositions according to the invention are presented in the form of oily, oleo-alcoholic, or aqueous-alcoholic lotions they may constitute, for example, sun-screen lotions containing a filter absorbing UV radiation or softening lotions for skin; the oily lotions may in addition constitute foam oils containing oil-soluble surfactant, bath oils, etc.

Among the principal adjuvants that may be present in compositions according to the invention one may cite organic or aqueous-glycolic solvents, including MP-diol and polyglycerols, fatty substances obtained by extraction or synthesis, ionic or non-ionic thickeners, softeners, opacifiers, stabilizers, emollients, silicones, α- or β-hydroxy acids, antifoaming agents, moisturizing agents, vitamins, perfumes, preservatives, sequestrating agents, colouring agents, gel-forming and viscosity-increasing polymers, surfactants and emulsifiers, other water- or fat-soluble active principles, plant extracts, tissue extracts, marine extracts, sun filters, and antioxidants.

The more particularly preferred mono- or poly-alcohols are chosen from among ethanol, isopropanol, propylene glycol, glycerol, and sorbitol.

As the fatty substance, among mineral oils one may cite liquid petrolatum; among animal oils whale oil, shark oil, seal oil, menhaden oil, halibut liver oil, cod liver oil, tunny-fish oil, turtle oil, neat's foot oil, horse foot oil, sheep's foot oil, mink oil, otter oil, marmot oil, etc.; and among vegetable oils almond oil, wheat germ oil, jojoba oil, sesame oil, sunflower seed oil, palm oil, walnut oil, shea nut oil, shorea oil, macadamia nut oil, blackcurrant seed oil, and the like.

Among the fatty acid esters useful as a fatty substance one may use esters of $C_{12}$ to $C_{22}$ acids, saturated or unsaturated, and lower alcohols such as isopropanol or glycerol or aliphatic $C_8$ to $C_{22}$ alcohols, straight-chain or branched, saturated or unsaturated, or $C_{10}$-$C_{22}$ alkane 1,2-diols.

As the fatty substance one may also cite petroleum, paraffin, waxes, lanolin, hydrogenated lanolin, tallow, acetylated lanolin, and silicone oils.

Among waxes one may cite Sipol wax, lanolin wax, beeswax, Candelilla wax, monocrystalline wax, Carnauba wax, spermaceti, cocoa butter, karite nut butter, silicone waxes, hydrogenated oils solidified at 25° C., sucroglycerides, oleates, myristates, linoleates, and stearates of calcium, magnesium, and aluminium.

Among the aliphatic alcohols one may cite lauryl alcohol, cetyl alcohol, myristyl alcohol, stearyl alcohol, palmityl alcohol, oleyl alcohol, and Guerbet's alcohols such as 2-decyltetradecanol or 2-hexyldecanol. As emulsifying agents among the aliphatic polyoxyethylenated alcohols one may cite lauryl, cetyl, stearyl, and oleyl alcohols containing 2 to 20 moles of ethylene oxide, and among the glycerol alkoyl ethers $C_{12}$-$C_{18}$ alcohols containing 2-10 moles of glycerol. It may also be useful to include thickeners such as cellulose derivatives, polyacrylic acid derivatives, guar gum, carouba gum, or xanthan gum.

The compositions according to the invention may include various other and additional, conventional ingredients or not. Of course a decision to include an additional ingredient and the choice of a specific active ingredient and additional ingredients depends on the specific application and the product formulation. Also the line of demarcation between an "active" ingredient and an "additional" ingredient is artificial and depends on the specific application and product type. A substance that is an "active" ingredient in one application or product may be an additional or "functional" ingredient an in another, and vice versa.

The composition according to the invention may thus include one or more active additional ingredients, which provide some benefit to the object of the application of the composition, for example the skin or the hair. Such additional ingredients may include one or more substances such as, cleaning agents, hair conditioning agents, skin conditioning agents, hair styling agents, antidandruff agents, hair growth promoters, perfumes, sunscreen and/or sunblock compounds, pigments, moisturizers, film formers, hair colors, make-up agent, detergents, thickening agents, emulsifying agents, antiseptic agents, deodorant actives, surfactant, propellant.

The choice of one or more active ingredients depends on the nature of the cosmetic product or skin care to formulate. For example, sun filters can be used in anti-sun lotions, shampoos, lotions of capillary care, and so on. For each type of active ingredient, one or more additives may be present. In the same way, more than one type of active ingredients may be present in a composition.

The *CTFA Cosmetic Ingredient Handbook*, Ninth Edition (2002) describes a wide variety of cosmetic ingredients, also referred to herein as principal adjuvants commonly used in the cosmetic industry, which are suitable for use in the compositions of the present invention.

Some examples of these principal adjuvants include: abrasives, absorbents, essential oils, astringents, anti-agglomerant agents, antifoaming agents, antimicrobial agents, binders, biological additives, buffering agents, bulking agents, chelating agents, chemical additives, cosmetic astringents, cosmetic biocides, denaturants, drug astringents, external analgesics, film formers opacifying agents, pH adjusters, propellants, reducing agents, sequestrants, skin-conditioning agents (e.g., humectants) skin treating agents, thickeners, but also active substances selected from the group formed by exfoliate actives, anti-acne actives, vitamin C and its derivatives, vitamins $B_1$ through $B_{12}$, and their derivatives, vitamin E and its derivatives, vitamin H, vitamin K, vitamin A and the retinoids, peptides, hydroxy acids, antioxidants, radicals quenchers, chelating agents, anti-inflammatory actives, tanning actives, skin bleaching actives, anti-cellulite actives, antimicrobial actives, anti-wrinkle actives, anti-lipolysis actives, lipogenesis stimulating actives, anti-stress agents, proteolysis inhibitors, in particular inhibitors of the MMP, enzymes, ceramides and their analogues, anti-irritants and actives softening the skin, anti-pollution actives, healing actives, hydrating, emollients, anti-sun protection actives, sunscreens and filters UV, firming actives, liposomes.

In particular, the capillary care ingredients that can be combined in the compositions according to the present invention can be found on www.sederma.fr, or in the paragraphs which follow.

The compositions according to the present invention can also contain a sufficient quantity of anti-acne actives. Examples of anti-acne actives include the composition called ac.net® (marketed by SEDERMA, France) and its individual components (nordihydroguaiaretic acid, oleanolic acid), and also resorcinol, sulphur, salicylic acid, benzoyl peroxide, erythromycin, zinc, etc. Other examples of anti-acne actives are described in details in U.S. Pat. No. 5,607, 980, granted to McAtee et al., Mar. 4, 1997.

The compositions of the present invention may further contain an effective amount of anti-wrinkle actives. Exemplary anti-wrinkle actives suitable for use in the compositions of the present invention include alpha-hydroxy acids such as lactic acid and glycolic acid or beta-hydroxy acids such as salicylic acid and salicylic acid derivatives, vitamins, in particularly vitamin $B_3$ and retinoids. Isoflavones and phytosterols are also particularly suitable.

Peptides, including, di-, tri-, tetra-, pentapeptides and derivatives thereof, may be included in the compositions of the present invention in amounts that are effective. As used herein, "peptides" refers to both the naturally occurring peptides and synthesized peptides. Suitable dipeptides for use herein include, but not limited to, Tyr-Arg, Val-Trp, Asn-Phe, Asp-Phe, beta-Ala-His (Carnosine), N-palmitoyl-beta-Ala-His, Tyr-Arg-hexadecylester, and theirs derivatives. Tripeptides include Gly-His-Lys, Arg-Lys-Arg, His-Gly-Gly, Lys-Phe-Lys, Lys-Phe-Lys and their analogues of conservative substitution Gly-His-Lys, Gly-Lys-His, Arg-Lys-Arg-$NH_2$, et theirs derivatives. Tetrapeptides include Gly-Gln-Pro-Arg (Rigin), Thr-Lys-Pro-Arg (Tuftsin) Lys-Asn-Pro-Tyr, Lys-Asn-Gly-Tyr, Lys-Asn-(D-Pro)-Tyr, Lys- Asn-Pro-Phe, (D-Lys)-Asn-Pro-Tyr, Lys-Gln-Pro-Tyr, Gly-Asn-Pro-(D-Arg), Gly-Asn-Pro-Tyr, (D-Lys)-Asn-Gly-Tyr, (D-Lys)-Gln-Pro-Tyr and (D-Lys)-Asn-Pro-Phe and theirs derivatives and their analogues of conservative substitution. Pentapeptides and hexapeptides for use herein include, but are not limited to Lys-Thr-Thr-Lys-Ser, Tyr-Gly-Gly-Phe-X with X=Met or Leu or mixture thereof, Val-Gly-Val-Ala-Pro-Gly and theirs derivatives. These peptides will be used in their free forms or N-acylated. A preferred dipeptide derivative is N-Acetyl-Tyr-Arg-hexadecylester (CAL-MOSENSINE® from SEDERMA, France). A preferred tripeptide is N-Palmitoyl-Gly-His-Lys (Pal-GKH from SEDERMA, France), Peptide CK (Arg-Lys-Arg) and Lipospondin (N-Elaidoyl-Lys-Phe-Lys) and its conservative substitution analogs, Peptide CK+ (N-Acetyl-Arg-Lys-Arg-NH$_2$. A preferred tetrapeptide is N-palmitoyl-Gly-Gln-Pro-Arg, and a preferred pentapeptide is N-Pal-Lys-Thr-Thr-Lys-Ser available as MATRIXYL® from SEDERMA, France.

The compositions of the present invention may include an effective amount of an anti-oxidant or a radical scavenger for providing protection against UV radiation. Anti-oxidants/radical scavengers such as ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts 6-hydroxy acid (commercially available under the tradename Trolox®) gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, methionine, proline, superoxide dismutase, Extremozymes like that proposed under the name VENUCEANE® (proposed by SEDERMA, France), silymarin, tea extracts, grape skin/seed extracts, melanin, and rosemary extracts may be used.

Flavonoids suitable for use in the present invention are flavanones selected from unsubstituted flavanones, mono-substituted flavanones, and mixtures thereof; chalcones selected from unsubstituted chalcones, mono-substituted chalcones, di-substituted chalcones, tri-substituted chalcones, and mixtures thereof; flavones selected from unsubstituted flavones, mono-substituted flavones, di-substituted flavones, and mixtures thereof; one or more isoflavones; coumarins selected from unsubstituted coumarins, mono-substituted coumarins, di-substituted coumarins, and mixtures thereof; chromones selected from unsubstituted chromones, mono-substituted chromones, di-substituted chromones, and mixtures thereof; one or more dicoumarols; one or more chromanones; one or more chromanols; isomers (e.g., cis/trans isomers) thereof; and mixtures thereof.

Other examples of flavonoids can be found in PCT application No WO 00/62743 filed by Larry R. Robinson et al. on Apr. 19, 2000, published on Oct. 26, 2000. They can be obtained like extracts of natural sources (plants, algae), like products of hemisynthesis or synthesis. Mixtures of flavonoid compounds above may also be used.

The compositions of the present invention may contain a skin lightening agent. Suitable skin lightening agents include kojic acid, arbutin, ascorbic acid and derivatives thereof (e.g., magnesium ascorbyl phosphate or sodium ascorbyl phosphate), and extracts (e.g. citrus unshiu extract, bearberry and mitracarpus extracts available as MELASLOW®, LUMISKIN® et ETIOLINE® of SEDERMA, France).

Anti-inflammatory agents may be added in compositions according to the present invention, like plant, fungi, algae natural extracts. For example, ursolic acid, nordihydroguaiaretic acid, kava-kava extract, bacopa monieri extract (BACOCALMINE® of SEDERMA, France), candelilla wax, bisabolol, aloe vera, plant sterols, chamomile, red clover extract (marketed under name STEROCARE® of SEDERMA, France), and sea whip extract, may be used.

When the compositions according to the invention are in the form of dispersions, these may be dispersions of lecithin in water in the presence of a surfactant or they may be aqueous dispersions of lipid spherules consisting of organized molecular layers enclosing an encapsulated aqueous phase. The lipid compounds may be long-chain alcohols and diols, sterols such as cholesterol, phospholipids, cholesteryl sulfate and phosphate, long-chain amines and their quaternary ammonium derivatives, dihydroxyalkylamines, poly-oxyethylenated aliphatic amines, long-chain amino alcohol esters, their salts and quaternary ammonium derivatives, phosphate esters of aliphatic alcohols such as hydrogen dicetyl phosphate or its sodium salt, alkyl sulfates such as sodium cetyl sulfate, fatty acids in the form of salts, or else lipids of the type of those described in French patents FR 2,315,991, FR 1,477,048, and FR 2,091,516 or in international patent applications WO 83/01571 and WO 92/08685.

As other lipids one may use, for example, lipids containing a lipophilic long chain of 12 to 30 carbon atoms, saturated or unsaturated, branched or straight-chain, for example an oleyl, lanolyl, tetradecyl, hexadecyl, isostearyl, lauryl, or alkoylphenyl chain. The hydrophilic group in these lipids may be ionic or non-ionic. The non-ionic groups may be groups derived from polyethylene glycol. One can also use advantageously, as lipids forming the lamellar phase, polyglycol ethers such as those described in French patents FR 1,477,048, FR 2,091,516, FR 2,465,780, and FR 2,482, 128.

The ionic group may advantageously be a group derived from an amphoteric, anionic, or cationic compound.

Some other lipids described in international patent application WO 83/01571 as suitable for the formation of vesicles are glycolipids such as lactosylceramide, galactocerebroside, gangliosides and trihexosylceramide, as well as phospholipids such as phosphatidylglycerol and phosphatidylinositol.

The active substances may be substances of nutritional or pharmaceutical interest or ones having a cosmetic activity. When they are water-soluble they may be dissolved to produce a homogeneous solution or they are in the aqueous phase encapsulated within the vesicles. The water-soluble substances having a cosmetic and/or pharmaceutical activity may be products intended for skin and hair care or treatment, such as for example moisturizers such as glycerol, sorbitol, pentaerythritol, pyrrolidine acid and its salts; artificial suntan agents such as dihydroxyacetone, erythrulose, glyceraldehyde, γ-dialdehydes such as tartaric aldehyde, these products being possibly associated with colouring agents; water-soluble sun filters; antiperspirants, deodorants, astringents, fresheners, tonics, healing products, keratolytics, depilatories, scents; plant tissue extracts such as polysaccharides; water-soluble colorants; anti-dandruff agents; antiseborrheic agents, oxidants such as bleaching agents, for example hydrogen peroxide; and reducing agents such as thioglycolic acid and its salts.

Mention can also be made of vitamins, hormones, enzymes such as superoxide dismutase, vaccines, antiinflammatories such as hydrocortisone, antibiotics, bactericidal agents, cytotoxic agents, or antitumour agents.

When the active substances are oil-soluble they may be incorporated in the walls of the vesicles. They may be chosen from the group formed by oil-soluble sun filters, substances intended for improving of the condition of dry or old skin, tocopherols, vitamins E, F, or A or their esters, retinoic acid, antioxidants, essential fatty acids, glycyrrhetinic acid, keratolytics, and carotenoids.

Compounds of general formula I, as well as cosmetic and dermopharmaceutical compositions containing the same, alone or in association, objects of the invention, may be used in cosmetic compositions in accordance with the invention either as individual additions or as a premix in a suitable carrier, and be in the form of solution, dispersion, emulsion, paste, or powder. They may be included individually or together in vehicles such as macro-, micro-, or nanocapsules, liposomes or chylomicrons, macro-, micro-, or nanoparticles or microsponges. They may also be adsorbed on organic polymer powders, talcs, bentonites, or other inorganic supports.

Compounds of general formula I as well as cosmetic and dermopharmaceutical compositions containing the same, alone or in association, may be used in any form whatsoever, or in a form bound to or incorporated in or absorbed in or adsorbed on macro-, micro-, and nanoparticles, or macro-, micro-, and nanocapsules, for the treatment of textiles, natural or synthetic fibres, wools, and any materials that may be used for clothing or underwear for day or night intended to come into contact with the skin, such as tights, underclothes, handkerchiefs, or cloths, to exert their cosmetic effect via this skin/textile contact and to permit continuous topical delivery.

The present invention also covers use of one or more compounds of general formula I including 2,9-dihydroxy-1,10-dimethoxy-6-methyl-noraporphine (formula I, $R^1$=H, $R^2$=$R^3$=$CH_3$, $R^4$=H, $R^5$=$CH_3$), 1,2,10-trimethoxy-9-hydroxy-6-methyl-noraporphine (formula I, $R^1$=$R^2$=$R^3$=$CH_3$, $R^4$=H, $R^5$=$CH_3$) and 1,2,9,10-tetramethoxy-6-methyl-noraporphine (formula I, $R^1$=$R^2$=$R^3$=$R^4$=$R^5$=$CH_3$), and use of cosmetic and dermopharmaceutical compositions containing one or more of said compounds alone or in association with a plant extract, in particular *glaucium* extract, like or for the preparation of cosmetic or dermopharmaceutical compositions with the aim of decreasing pigmentation, in particular to lighten the complexion, attenuate senile lentigo, homogenize skin color, or lighten any pigmentation associated with melanin, including that of the hair or in the objective of an anti-age treatment, anti-ageing, antiradicalaire, antioxydant treatment, or in the objective of a slimming, a reduction of the orange peel and/or overloads of the thighs and the hips, anti-cellulite treatment, skin firming, to refine contours of the face, more generally the lipogenesis inhibition.

Compounds of general formula I as well as cosmetic and dermopharmaceutical compositions, including said compounds alone or in a association, may be used in the preparation of medicinal products intended for skin care, particularly skin lightening and reducing its coloration under exposure to natural or artificial UV radiation or in the objective of an anti-age, anti-ageing, antiradicalaire, antioxydant treatment, or in the objective of a slimming treatment, a reduction of the orange peel and/or overloads of the thighs and the hips, an anti-cellulite treatment, skin firming, more generally the lipogenesis inhibition.

Moreover, the substances and compositions that are the subject of the present patent may be used to manufacture cloth, textiles and clothing with a cosmetic effect, in particular for lightening the skin or hair, or to act against the time effects, or to thin, reduce the orange skin.

Examples are given below as a non-restrictive illustration of implementation of the present invention.

EXAMPLE NO. 1

Synthesis of 2,9-diacetyloxy-1,10-dimethoxy-6-methyl-noraporphine (Compound II)

To a solution of 2,9-dihydroxy-1,10-dimethoxy-6-methyl-noraporphine (1.01 g; 3.09 mmol) in 20 ml of dichloromethane (DCM) are successively added, at room temperature, 3.09 equivalents of acetic anhydride ($Ac_2O$) (900 µl; 9.5 mmol) then 1.99 equivalent of diisopropylethylamine (DIEA) (1.05 ml; 6.13 mmol). After one night of stirring at room temperature in the dark, oil ether (50 ml) and water (50 ml) are added. After extraction, the organic phase is dried on anhydrous sodium sulphate (5 g), is filtered and is evaporated. 1.15 g (2.795 mmol; 90.5% of 2,9-diacetyloxy-1,10-dimethoxy-6-methyl-noraporphine are isolated in as an odorless yellow solid after one night of drying in the desiccator.

To a solution of 2,9-dihydroxy-1,10-dimethoxy-6-methyl-noraporphine (1.01 g; 3.09 mmoles) in 20 ml of dichloromethane (DCM) are successively added, at room temperature, 3.09 equivalents of acetic anhydride ($Ac_2O$) (900 µl; 9.52 mmoles) then 1.99 equivalents of diisopropylethylamine (DIEA) (1.05 ml; 6.13 mmols). After one night of stirring at room temperature in the dark, oil ether (50 ml) and water (50 ml) are added. After extraction, the organic phase is dried on anhydrous sodium sulphate (5 g), is filtered and is evaporated. 1.15 g (2.795 mmoles; 90.5%) of 2,9-diacetyloxy-1,10-dimethoxy-6-methyl-noraporphine are isolated in as an odourless yellow solid after one night of drying to the desiccator $C_{23}H_{25}NO_6$ MM=411.4588 gmol$^{-1}$ Melting Point: 80-81° C.

CHN: Calculated: 67.14% C; 6.12% H; 3.40% N

Found: 67.26% C; 6.07% H; 3.38% N

Infra Red: 2955; 2895; 2835; 2789; 1766; 1695; 1515; 1462; 1421; 1368; 1316; 1199; 1079; 1000; 906 cm$^{-1}$.

Mass spectrometry: (m/z)=412.4 [M+H]$^+$

| Example No. 2 | |
|---|---|
| Day Cream | g/100 g |
| Volpo S20 | 2.4 |
| Volpo S2 | 2.6 |
| Prostearyl 15 | 8.0 |
| Beeswax | 0.5 |
| Stearoxydimethicone | 3.0 |
| Propyleneglycol | 3.0 |
| Carbomer | 0.25 |
| Triethanolamine | 0.25 |

-continued

Example No. 2

| Day Cream | g/100 g |
|---|---|
| 2, 9-diacetyloxy-1, 10-dimethoxy-6-methyl-noraporphine | $2.5 \cdot 10^{-3}$ |
| Water, preservatives, fragrance | qsp 100 g |

This emulsion is used to lighten and moisturize face skin.

Example No. 3

| Slimming Gel | g/100 g |
|---|---|
| Carbopol 1342 | 0.3 |
| Propylene glycol | 2.0 |
| Glycerin | 1.0 |
| White petrolatum | 1.5 |
| Cylomethicone | 6.0 |
| Cetylic alcohol | 0.5 |
| Lubrajel MS | 10.0 |
| Triethanolamine | 0.3 |
| 2, 9-diacetyloxy-1, 10-dimethoxy-6-methyl-noraporphine | 0.01 |
| Water, preservatives, fragrance | qsp 100 g |

Example No. 4

| Massage slimming cream | g/100 |
|---|---|
| Ultrez 10 | 0.2 |
| Butylene glycol | 5.0 |
| Stearic acid | 1.5 |
| Crodamol GTCC | 2.0 |
| Petrolatum oil | 2.0 |
| Crodacol C90 | 0.5 |
| Crodafos CES | 1.5 |
| *Glaucium flavum* extract | 3.0 |
| Water, preservatives, fragrance | qsp 100 g |

EXAMPLE NO. 5

Inhibition of Melanin Synthesis (In Vitro)

The efficacy of the products on melanization was tested in culture of normal human melanocytes (MHN). This culture medium is conventionally used to test variations in melanin levels. The cells are incubated in the presence of the test product for 7 days while the control cells are incubated in the culture medium alone.

After 7 days, the total melanin (phaeomelanin and eumelanin) present in the cells is determined after cell lysis and dissolution in sodium hydroxide, the assay is colorimetric.

The melanin level produced under exposure to the test product at various concentrations are compared to those obtained with the control cells. The data are normalized on the protein content of the sample.

Figure 1:
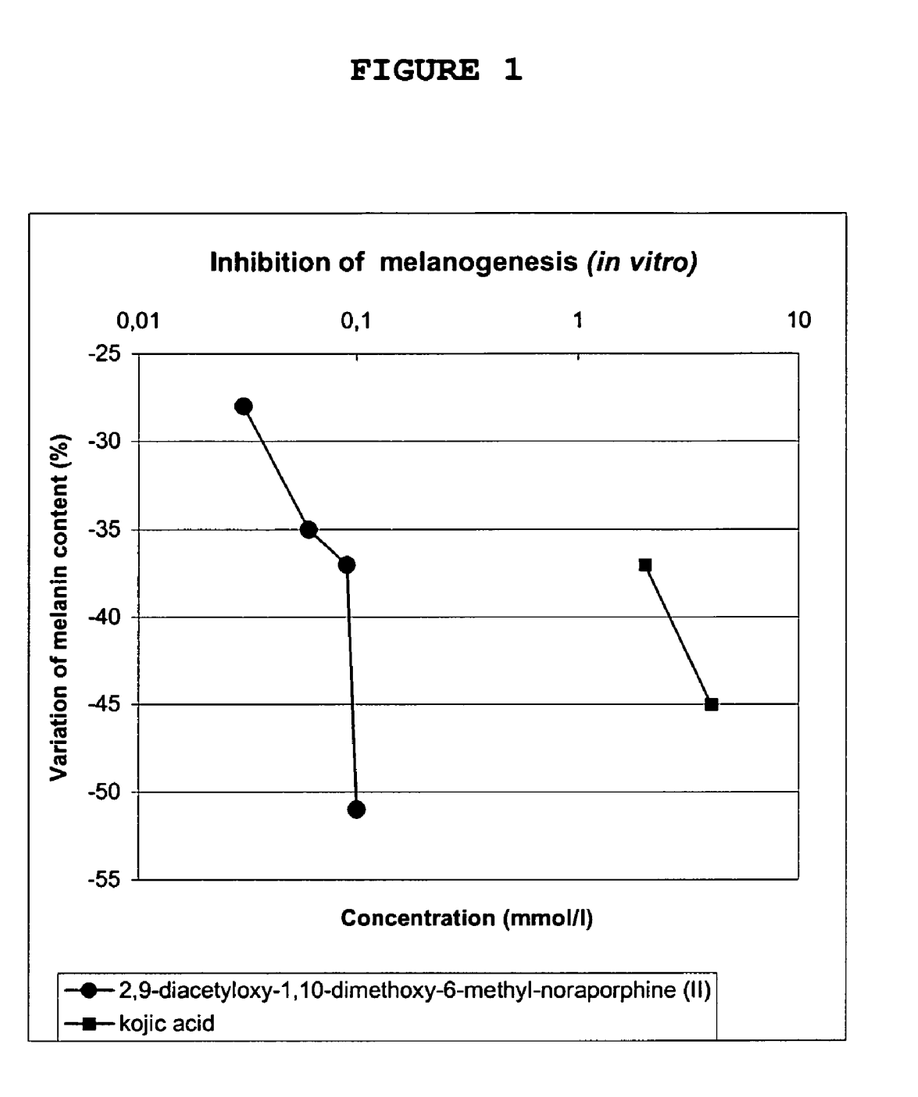
FIG. 1 illustrates the inhibition of melanogenesis (in vitro) of 2,9-diacetyloxy-1,10-dimethoxy-6-methyl-noraporphine and kojic acid.

The single figure shows the variation in melanin synthesis under exposure to kojic acid for 7 days (positive control), on the one hand, and under exposure to 2,9-diacetyloxy-1,10-dimethoxy-6-methyl-noraporphine (compound II), object of the present demand on the other hand. The inhibition of synthesis observed after 7 days of exposure to those products is dependent on the test concentration. Inhibition varies from −28 to −51%. This demonstrates that this compound has a very interesting inhibitory activity on melanogenesis.

EXAMPLE NO. 6

Inhibition of Lipogenesis (In Vitro)

The following test is based on the fact that a cocktail from substances (hormonal messengers) induce the fibroblasts 3T3 L1 differentiation, in culture, into pre-adipocytes then in adipocytes charged with lipids.

The culture proceeds in three stages: cellular multiplication until confluence, addition of cocktail of differentiation (stage during which the initial pre-adipocytes are obtained (72 hours), then active differentiation with lipogenesis stimulation (approximately 72 hours) at the end of which apparent storage in lipidic droplets is then definitely visible under microscope.

The enzyme G-3-PDH (Glycerol-3-Phosphate deshydrogenase), essential to triglyceride synthesis is expressed very strongly during this active stage of lipidic storage.

The product to be tested is added at the second step.

After the incubation period the G-3-PDH activity is compared between the pre-adipocytes witnesses and those incubated in the presence of the tested product. Under these conditions, a product which inhibits the lipogenesis causes a fall of the G-3-PDH activity.

Followed Protocol

After the induced differentiation, the solution to test is added to the culture of pre-adipocytes, here a 2,9-diacetyloxy-1,10-dimethoxy-6-methyl-noraporphine solution (compound II). In parallel, two witness cultures, one in negative and the other in positive are carried out.

At the end of the incubation, the cells are taken and lysed and the test is carried out on the intracellular contents.

The G-3-PDH activity is measured by NADH disappearance ($\lambda$=340 nm).

Inhibition of the G-3-PDH Activity:

The following table shows the averages of the measurements (inhibition—in % of the witness—G-3-PDH activity in cultured pre-adipocytes treated by 2,9-diacetyloxy-1,10-dimethoxy-6-methyl-noraporphine, compound II) realized with 3 tests independent to each other. The enzymatic activity values are standardized with the number of cells.

| | ACTIVITY G-3-PDH/$10^{-6}$ cells |
|---|---|
| II - 0.03 mmol/l | −49% |
| II - 0.06 mmol/l | −67% |
| II - 0.09 mmol/l | −76% |

These results clearly show 2,9-diacetyloxy-1,10-dimethoxy-6-methyl-noraporphine (compound II) effect on the G-3-PDH activity, as an G-3-PDH inhibition of 76% approximately is obtained in the presence of only 0.09 mmol/l compound II. Moreover, this effect is incontestably concentration-dependent.

The G-3-PDH significant inhibition shows 2,9-diacetyloxy-1,10-dimethoxy-6-methyl-noraporphine (compound II) inhibiting capacity on the lipogenesis in the preadipocytes.

Morphology of the Preadipocytes:

The cell morphology under microscope shows an adipocyte population with few lipidic inclusions compared to witness cells.

EXAMPLE 7

Inhibition of Poroxydation Perixodiation (In Vitro)

In order to seek an antioxidant activity, we evaluated 2,9-diacetyloxy-1,10-dimethoxy-6-methyl-noraporphine (compound II) effect on the inhibition of peroxidation induced on liposomes by UVA or pair $HO_2/FeCl_2$.

The liposomes, once manufactured, receive the products to be tested in solution. Then they are put under UVA lamp and are irradiated to 10 J/cm². The liposomes are incubated at 45° C. After 24 hours, the lipidic peroxidation is quantified by estimating the rate of combined dienes markers. The effect of the product is compared with negative control.

|  | Inhibition perox. UVA |
| --- | --- |
| II - 0.03 mmol/l | −93% |
| II - 0.06 mmol/l | −87% |
| II - 0.09 mmol/l | −89% |
| II - 0.15 mmol/l | ≈−100% |
| II - 0.30 mmol/l | ≈−100% |

With the tested concentrations, 2,9-diacetyloxy-1,10-dimethoxy-6-methyl-noraporphine (compound II) almost completely inhibits lipidic peroxidation UVA induced.

$HO_2/FeCl_2$.

A strong inhibition (−60% with 0.06 mmol/l) is also obtained in a similar protocol when $HO_2/FeCl_2$. is added (Fenton reaction) to the solution of liposomes.

The invention claimed is:

1. A method of decreasing pigmentation in a person in need thereof comprising the steps of: providing a topical cosmetic or dermopharmaceutical composition comprising a compound selected from the group consisting of 2,9-dihydroxy-1,10-dimethoxy-6-methyl-noraporphine, 1,2,10-trimethoxy-9-hydroxy-6-methyl-noraporphine, 2,9-diacetyloxy-1,10-dimethoxy-6-methyl-noraporphine and 1,2,9,10-tetramethoxy-6-methyl-noraporphine, and cosmetically acceptable salts thereof, and optical isomers thereof, and a carrier; and applying said compound to the skin of a person in need thereof.

2. A method of slimming, reducing cellulite or firming the skin of a person in need thereof comprising the steps of:

providing a topical cosmetic or dermopharmaceutical composition comprising a compound selected from the group consisting of 1,2,10-trimethoxy-9-hydroxy-6-methyl-noraporphine, 2,9-diacetyloxy-1,10-dimethoxy-6-methyl-noraporphine and 1,2,9,10-tetramethoxy-6-methyl-noraporphine and cosmetically acceptable salts thereof, and optical isomers thereof, and a carrier; and applying said compound to the skin of a person in need thereof.

3. The method of claim 1 or 2 wherein said compound is present at a concentration between 0.0001 (w/w) and 50% (w/w).

4. The method of claim 3 wherein said compound is present at a concentration between 0.0001 (w/w) and 20% (w/w).

5. The method of claim 3 wherein said compound is present in the form of a solution, dispersion, emulsion, paste, or powder, or is included individually or as a premix in vehicles constituted by carriers such as macro-, micro-, or nanocapsules, liposomes or chylomicrons, macro-, micro-, or nanoparticles or microsponges, or are adsorbed on organic polymers powders, talcs, bentonites, or other inorganic supports.

6. The method of claim 3 wherein said composition is a foundation, tint base, sun-screen, suntan lotion, milk, or cream, shaving cream, shaving foam, aftershave, shampoo, lipstick, mascara, or nail varnish.

* * * * *

UNITED STATES PATENT AND TRADEMARK OFFICE
CERTIFICATE OF CORRECTION

PATENT NO. : 7,354,926 B2
APPLICATION NO. : 10/525985
DATED : April 8, 2008
INVENTOR(S) : Karl Lintner It is certified that error appears in the above-identified patent and that said Letters Patent is hereby corrected as shown below:

Column 12, line 21, "(900 µl; 9.5" should read -- (900 µl; 9.52 --.
Please delete the paragraph at Column 12, lines 31-43.
Column 15, line 8, "Inhibition of Poroxydation Perixodiation (In Vitro)" should read -- Inhibition of Peroxidation (In Vitro) --.
Column 16, line 26, "between 0.0001 (w/w) and 20%" should read -- between 0.001 (w/w) and 20% --.

Signed and Sealed this

Twelfth Day of August, 2008

JON W. DUDAS
*Director of the United States Patent and Trademark Office*